(12) United States Patent
Nappa et al.

(10) Patent No.: US 8,133,406 B2
(45) Date of Patent: Mar. 13, 2012

(54) PROCESSES FOR PRODUCING 2,3,3,3-TETRAFLUOROPROPENE AND/OR 1,2,3,3-TETRAFLUOROPROPENE

(75) Inventors: Mario Joseph Nappa, Newark, DE (US); Velliyur Nott Mallikarjuna Rao, Wilmington, DE (US); Allen Capron Sievert, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 136 days.

(21) Appl. No.: 12/446,063

(22) PCT Filed: Oct. 31, 2007

(86) PCT No.: PCT/US2007/022992
§ 371 (c)(1),
(2), (4) Date: Apr. 17, 2009

(87) PCT Pub. No.: WO2008/054779
PCT Pub. Date: May 8, 2008

(65) Prior Publication Data
US 2010/0320412 A1    Dec. 23, 2010

Related U.S. Application Data

(60) Provisional application No. 60/855,484, filed on Oct. 31, 2006.

(51) Int. Cl.
*C09K 5/04* (2006.01)
*C11D 7/30* (2006.01)
*C07C 17/25* (2006.01)
(52) U.S. Cl. .......... 252/67; 510/412; 570/155; 570/156; 570/160
(58) Field of Classification Search .......... 252/67; 510/412; 570/155, 156, 160
See application file for complete search history.

(56) References Cited

U.S. PATENT DOCUMENTS

| | | | |
|---|---|---|---|
| 5,629,461 A | 5/1997 | Yasuhara et al. | |
| 5,756,869 A | 5/1998 | Yoshikawa et al. | |
| 7,872,161 B2 * | 1/2011 | Rao et al. | 570/176 |
| 7,981,312 B2 * | 7/2011 | Nappa et al. | 252/67 |
| 2003/0060669 A1 * | 3/2003 | Shibata et al. | 570/136 |
| 2005/0090698 A1 | 4/2005 | Merkel et al. | |
| 2006/0106263 A1 | 5/2006 | Miller et al. | |
| 2006/0217577 A1 | 9/2006 | Mukhopadhyay | |
| 2007/0096053 A1 | 5/2007 | Nair et al. | |
| 2007/0100175 A1 | 5/2007 | Miller et al. | |
| 2007/0129579 A1 | 6/2007 | Wang et al. | |
| 2008/0027251 A1 * | 1/2008 | Nair et al. | 570/176 |
| 2010/0025620 A1 * | 2/2010 | Nappa et al. | 252/67 |
| 2010/0294979 A1 * | 11/2010 | Sievert | 252/67 |
| 2011/0178344 A1 * | 7/2011 | Nose et al. | 570/160 |
| 2011/0251442 A1 * | 10/2011 | Okamoto et al. | 570/156 |

FOREIGN PATENT DOCUMENTS

| | | |
|---|---|---|
| WO | 2006094303 | 9/2006 |
| WO | 2008030444 | 3/2008 |
| WO | 2008054780 | 5/2008 |

OTHER PUBLICATIONS

Haszeldine & Steele, Journal of Chemical Society, pp. 2193-2197 (1957).

* cited by examiner

*Primary Examiner* — Douglas Mc Ginty

(57) ABSTRACT

A process is disclosed for making $CF_3CF=CH_2$ or mixtures thereof with $CHF_2CF=CHF$. This process involves (a) reacting $CHCl_2CF_2CF_3$, and optionally $CHClFCF_2CClF_2$, with $H_2$ in the presence of a catalytically effective amount of a hydrogenation catalyst to form $CH_3CF_2CF_3$ and, when $CHClFCF_2CClF_2$ is present, $CH_2FCF_2CHF_2$; (b) dehydrofluorinating $CH_3CF_2CF_3$, and optionally any $CH_2FCF_2CHF_2$, from (a) to form a product mixture including $CF_3CF=CH_2$ and, if $CH_2FCF_2CHF_2$ is present, $CHF_2CF=CHF$; and optionally (c) recovering $CF_3CF=CH_2$, or a mixture thereof with $CHF_2CF=CHF$ from the product mixture formed in (b) and/or (d) separating at least a portion of any $CHF_2CF=CHF$ in the product mixture formed in (b) from the $CF_3CF=CH_2$ in the product mixture formed in (b).

2 Claims, No Drawings

PROCESSES FOR PRODUCING 2,3,3,3-TETRAFLUOROPROPENE AND/OR 1,2,3,3-TETRAFLUOROPROPENE

FIELD OF THE INVENTION

The present invention relates to processes that involve the production of halogenated hydrocarbon products comprising 2,3,3,3-tetrafluoropropene and/or 1,2,3,3-tetrafluoropropene.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a ($CF_3CH_2F$) being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

2,3,3,3-Tetrafluoropropene ($CH_2$=$CFCF_3$, HFC-1234yf) and 1,2,3,3-tetrafluoropropene ($CHF$=$CFCHF_2$, HFC-1234ye), both having zero ozone depletion and low global warming potential, have been identified as a potential components in refrigerant blends (see PCT WO 2006/094303). HFC-1234yf has been prepared by reaction of $CH_2ClC_2F_5$ with zinc in ethanol as reported by Haszeldine and Steele in Journal of the Chemical Society, pages 2193-2197 (1957). HFC-1234ye has been prepared as a by-product in the vapor phase fluorination of 3-chloro-1,1,2,2-tetrafluoropropane over a chromium catalysts as disclosed by Yasuhara, et. al. in U.S. Pat. No. 5,629,461. There is a need for new manufacturing processes for the production of HFC-1234yf and HFC-1234ye.

SUMMARY OF THE INVENTION

The present invention provides a process for making HFC-1234yf or mixtures thereof with HFC-1234ye. This process comprises (a) reacting HCFC-225ca ($CHCl_2CF_2CF_3$) and optionally HCFC-225cb ($CHClFCF_2CClF_2$) with $H_2$ in the presence of a catalytically effective amount of a hydrogenation catalyst to form $CH_3CF_2CF_3$ (HFC-245cb) and, when HCFC-225cb is present, $CH_2FCF_2CHF_2$ (HFC-245ca); (b) dehydrofluorinating HFC-245cb, and optionally any HFC-245ca, from (a) to form a product mixture comprising HFC-1234yf and, if HFC-245ca is present, HFC-1234ye; and optionally (c) recovering HFC-1234yf, or a mixture thereof with HFC-1234ye, from the product mixture formed in (b); and optionally (d) separating at least a portion of any HFC-1234ye in the product mixture formed in (b) from the HFC-1234yf in the product mixture formed in (b).

DETAILED DESCRIPTION

The present invention provides a process for making HFC-1234yf or mixtures thereof with HFC-1234ye. HFC-1234ye may exist as one of two configurational isomers, E- or Z-. HFC-1234ye as used herein refers to either E-HFC-1234ye (CAS Reg No. [115781-19-6]) or Z-HFC-1234ye (CAS Reg. No. [730993-62-1]), as well as any combination or mixture of such isomers.

The process comprises (a) reacting $C_3HCl_2F_5$ with $H_2$ in a reaction zone in the presence of a catalytically effective amount of hydrogenation catalyst to form $C_3H_3F_5$ (that is, the total of HFC-245cb and any HFC-245ca); and (b) dehydrofluorinating $C_3H_3F_5$ from (a) to form HFC-1234. In step (a) of this process of the invention, $C_3HCl_2F_5$ is reacted with hydrogen in the presence of a hydrogenation catalyst. Hydrogenation catalysts suitable for use in this invention include catalysts comprising at least one catalytic metal component selected from the group consisting of iron, cobalt, rhodium, nickel, palladium, and platinum. Said catalytic metal component is typically supported on a carbonaceous carrier such as activated carbon or graphite.

Of note are embodiments wherein the $C_3HCl_2F_5$ component (that is, the total of HCFC-225ca and HCFC-225cb) reacted with hydrogen is primarily HCFC-225ca.

Mixtures of HCFC-225ca and HCFC-225cb can be prepared by the reaction of dichlorofluoromethane (HCFC-21) with tetrafluoroethylene (TFE) in the presence of aluminum chloride as reported by Paleta, et. al. in Collections of Czechoslovia Chemical Communications, Vol. 36, pages 1867 to 1875 (1971) or by the reaction of dichlorofluoromethane (HCFC-21) with tetrafluoroethylene (TFE) in the presence of aluminum chlorofluoride as disclosed by Sievert, et. al. in U.S. Pat. No. 5,157,171.

Catalysts suitable for the hydrogenation step include those comprising palladium, optionally together with additional Group VIII metals (e.g., Pt, Ru, Rh or Ni). The palladium may be supported on alumina, fluorided alumina, aluminum fluoride or a mixture thereof; or may be supported on carbon. The palladium-containing precursor used to prepare the catalyst is preferably a palladium salt (e.g., palladium chloride). Other metals, when used, may be added to the support during the preparation of the catalyst.

The supported metal catalysts may be prepared by conventional methods known in the art such as by impregnation of the carrier with a soluble salt of the catalytic metal (e.g., palladium chloride or rhodium nitrate) as described by Satterfield on page 95 of Heterogenous Catalysis in Industrial Practice, $2^{nd}$ edition (McGraw-Hill, New York, 1991). Palladium supported on alumina is available commercially. Another suitable procedure for preparing a catalyst containing palladium on fluorided alumina is described in U.S. Pat. No. 4,873,381, which is incorporated herein by reference.

By a catalytically effective amount is meant the concentration of catalysts on the support that is sufficient to carry out the catalytic reaction. The concentration of palladium on the support is typically in the range of from about 0.1% to about 10% by weight based on the total weight of the catalyst and is preferably in the range of about 0.1% to about 5% by weight based on the total weight of the catalyst. The concentration of the additional Group VIII metal, when used, is about 3% by weight, or less, based on the total weight of the catalyst; but palladium is ordinarily at least 50% by weight based on the weight of the total metals present on the support, and preferably at least 80% by weight based on the weight of the total metals present on the support.

Of note are carbon-supported catalysts in which the carbon support has been washed with acid and has an ash content below about 0.1% by weight. Hydrogenation catalysts supported on low ash carbon are described in U.S. Pat. No. 5,136,113, the teachings of which are incorporated herein by reference. Of particular note are palladium catalysts supported on carbon (see e.g., U.S. Pat. No. 5,523,501, the teachings of which are incorporated herein by reference). Also of particular note are palladium catalysts supported on three-dimensional matrix porous carbonaceous materials. Preparation of such three-dimensional matrix porous carbonaceous materials is disclosed in U.S. Pat. No. 4,978,649, incorporated herein by reference.

The relative amount of hydrogen contacted with $C_3HCl_2F_5$ is typically from about one mole of hydrogen per mole of $C_3HCl_2F_5$ to about 15 moles of $H_2$ per mole of the $C_3HCl_2F_5$ starting material. Suitable reaction temperatures are typically from about 100° C. to about 350° C., preferably from about 200° C. to about 350° C. The contact time is typically from about 1 to about 450 seconds, preferably from about 10 to about 120 seconds. The reactions are typically conducted at atmospheric pressure or superatmospheric pressure.

The effluent from the reaction zone used for step (a) typically includes HCl, unreacted hydrogen, HFC-245cb, and one or more of CFC-1214ya and HCFC-235cb (normally HCFC-235cb without significant CFC-1214ya). The effluent may also contain HFC-1234yf, and HFC-263fb. If HCFC-225cb is present as a starting material, the effluent from the reaction zone typically also includes HFC-245ca and one or more of $CH_2FCF_2CClF_2$ (HCFC-235cc), HCFC-235ca, and CFC-1214yb (normally HCFC-235cc and HCFC-235ca without significant CFC-1214yb).

In one embodiment of the invention, the HFC-245cb is isolated by separation processes known in the art such as distillation; and the isolated HFC-245cb, essentially free of HFC-245ca, is then used for step (b) of the process to prepare HFC-1234yf. Unreacted $C_3HCl_2F_5$ and intermediate products such as $C_3H_2ClF_5$ isomers may be recycled to step (a) of the process. Reaction by-products such as $C_3Cl_2F_4$ isomers may be recovered and converted to HFC-1234 in the reaction zone of step (a) of the process or separately by contact with hydrogen in the presence of a hydrogenation catalyst.

In another embodiment of the invention, the $C_3HCl_2F_5$ is reacted with hydrogen in the presence of catalyst in a molar ratio of $H_2$ to $C_3HCl_2F_5$ of from about 1:1 to about 15:1; and, after separation of hydrogen chloride and any hydrogen, the remaining effluent from the reaction zone is then sent directly to step (b) of the process.

In step (b) of the process of the invention, the $C_3H_3F_5$ produced in step (a) is contacted with a dehydrofluorination catalyst in a reaction zone for time sufficient to convert at least a portion of the $C_3H_3F_5$ to HFC-1234yf and, if HFC-245ca is fed to the reaction zone, HFC-1234ye. The dehydrofluorination reaction may be conducted in a tubular reactor in the vapor phase at temperatures of from about 200° C. to about 500° C. and preferably from about 300° C. to about 450° C. The contact time is typically from about 1 to about 450 seconds, preferably from about 10 to about 120 seconds.

The reaction pressure can be subatmospheric, atmospheric or superatmospheric. Generally, near atmospheric pressures are preferred. However, the dehydrofluorination of $C_3H_3F_5$ can be beneficially run under reduced pressure (i.e., pressures less than one atmosphere).

The catalytic dehydrofluorination can optionally be carried out in the presence of an inert gas such as nitrogen, helium or argon. The addition of an inert gas can be used to increase the extent of dehydrofluorination. Of note are processes where the mole ratio of inert gas to $C_3H_3F_5$ is from about 5:1 to 1:1. Nitrogen is the preferred inert gas.

Typical dehydrofluorination reaction conditions and dehydrofluorination catalysts are disclosed in U.S. Pat. No. 5,396,000, which is herein incorporated by reference in its entirety. Preferably, the dehydrofluorination catalyst comprises at least one catalyst selected from the group consisting of carbon, aluminum fluoride, fluorided alumina, and trivalent chromium oxide.

Other dehydrofluorination catalysts useful for converting $C_3H_3F_5$ from step (a) to HFC-1234 products are described in U.S. Pat. No. 6,093,859; the teachings of this disclosure are incorporated herein by reference. Still other dehydrofluorination catalysts suitable for use in step (b) are described in U.S. Pat. No. 6,369,284; the teachings of this disclosure are incorporated herein by reference.

The products from the step (b) reaction zone typically include HF, HFC-1234yf, and when HFC-245ca is present, the E- and Z-forms of HFC-1234ye. Unconverted $C_3H_3F_5$ may be recovered and recycled back to the dehydrofluorination reactor to produce additional quantities of HFC-1234. The separation steps involving recovery of HFC-1234yf and/or HFC-1234ye, such as steps (c) and (d) above, can be carried out using conventional separation technology such as distillation.

Of note are processes wherein in step (a), the $C_3HCl_2F_5$ contacted with $H_2$ includes HCFC-225cb; wherein the $C_3H_3F_5$ dehydrofluorinated in (b) includes HFC-245ca; and wherein the product mixture formed in (b) includes HFC-1234ye. Included are processes wherein HFC-1234yf essentially free of HFC-1234ye is recovered and/or HFC-1234ye essentially free of HFC-1234yf is recovered.

Also of note are embodiments where HFC-1234yf is a desired product, and is recovered from the product mixture of step (b). The HFC-1234yf present in the effluent from the reaction zone may be separated from the other components of the product mixture and unreacted starting materials by conventional means (e.g., distillation). When HF is present in the effluent, this separation can also include isolation of azeotrope or near azeotrope composition of HFC-1234yf and HF and further processing to produce HF-free HFC-1234yf by using procedures similar to that disclosed in U.S. Patent Application No. 2006/0106263, which is incorporated herein by reference.

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

EXAMPLES

| LEGEND | |
|---|---|
| 225ca is $CF_3CF_2CHCl_2$ | 225cb is $CClF_2CF_2CHClF$ |
| 235ca is $CHClFCF_2CHF_2$ | 235cb is $CH_2ClCF_2CF_3$ |
| 235cc is $CH_2FCF_2CClF_2$ | 245ca is $CHF_2CF_2CH_2F$ |
| 245cb is $CF_3CF_2CH_3$ | 254eb is $CF_3CHFCH_3$ |
| 263fb is $CF_3CH_2CH_3$ | 1214ya is $CF_3CF=CCl_2$ |
| 1214yb is $CClF_2CF=CClF$ | 1234ye is $CHF_2CF=CHF$ |
| 1234yf is $CF_3CF=CH_2$ | |

Example 1

Synthesis of $CF_3CF=CH_2$ by Dehydrofluorination with Fluorided Alumina Catalyst A Hastelloy™ tube reactor (2.54 cm OD×2.17 cm ID×24.1 cm L) was filled with 25 cc of gamma-alumina ground to 12-20 mesh (0.84 to 1.68 mm). The catalyst was activated by heating at 200° C. for 15 minutes under a nitrogen purge and then reacted with a $HF/N_2$ mixture heated up to 425° C. to yield 16.7 gm of activated fluorided alumina.

At a temperature of 350° C., 10 sccm of nitrogen ($1.7 \times 10^{-7}$ $m^3/s$) and 15 sccm ($2.5 \times 10^{-7}$ $m^3/s$) of $CF_3CF_2CH_3$ were mixed and flowed through the reactor. The temperature was then raised to 400° C., the flow rates held constant. The effluent for both temperatures was sampled and analyzed by $^{19}$F NMR. Additionally, the effluent was analyzed by GC to determine concentrations as listed in Table 1.

TABLE 1

| Temp., °C. | N$_2$ flow (sccm) | CF$_3$CF$_2$CH$_3$ flow (sccm) | Concentrations, (Mole %) | | |
|---|---|---|---|---|---|
| | | | CF$_3$CF=CH$_2$ | CF$_3$CF$_2$CH$_3$ | Unks |
| 350 | 10 | 15 | 84.2 | 12.8 | 3.0 |
| 400 | 10 | 15 | 91.3 | 1.9 | 6.8 |

Unks = unknowns

Example 2

Synthesis of CF$_3$CF=CH$_2$ with Carbon Catalyst

A Hastelloy™ tube reactor (2.54 cm OD×2.17 cm ID×24.1 cm L) was filled with 25 cc (14.32 g) of Sibunit2 carbon beads. The catalyst was activated by heating at about 300° C. under a nitrogen purge.

Following the procedure of Example 1, a mixture of 10 sccm (1.7×10$^{-7}$ m$^3$/s) of nitrogen and 15 sccm (2.5×10$^{-7}$ m$^3$/s) of CF$_3$CF$_2$CH$_3$ were passed through the reactor giving a contact time of 60 seconds. The flows were reduced to 5 sccm (8.3×10$^{-8}$ m$^3$/s) of nitrogen and 7.5 sccm (1.3×10$^{-7}$ m$^3$/s) of CF$_3$CF$_2$CH$_3$ giving a contact time of 120 seconds. The effluent was sampled under both sets of conditions and analyzed by $^{19}$F NMR. The effluent compositions as determined by GC are listed in Table 2.

TABLE 2

| Temp., °C. | N$_2$ flow (sccm) | CF$_3$CF$_2$CH$_3$ flow (sccm) | Concentrations, Mole % | | |
|---|---|---|---|---|---|
| | | | CF$_3$CF=CH$_2$ | CF$_3$CF$_2$CH$_3$ | Unks |
| 400 | 10 | 15 | 6.0 | 93.9 | 0.1 |
| 400 | 5 | 7.5 | 22.8 | 76.4 | 0.8 |

Unks = unknowns

Example 3

Synthesis of CHF$_2$CF=CHF from CHF$_2$CF$_2$CH$_2$F

A 0.375 inch (0.95 cm) O.D. Hastelloy™ nickel alloy tube was charged with 7.0 grams (10 cc) of gamma-alumina ground to 12/20 mesh (0.84 to 1.68 mm). The tube was purged with nitrogen (50 sccm, 8.3×10$^{-7}$ m$^3$/s) for twenty minutes as the temperature was raised from 40° C. to 175° C. The nitrogen flow was continued as anhydrous hydrogen fluoride (50 sccm, 8.3×10$^{-7}$ m$^3$/s) was added to the reactor for about 1.5 hours. The nitrogen flow was then reduced to 20 sccm (3.3×10$^{-7}$ m$^3$/s) and the hydrogen fluoride flow increased to 80 sccm (1.3×10$^{-6}$ m$^3$/s) as the temperature in the tube was increased from 174° C. to 373° C. over the course of 3.7 hours. The nitrogen flow was then reduced to 10 sccm (1.7×10$^{-7}$ m$^3$/s) and the hydrogen fluoride flow was maintained at 80 sccm (1.3×10$^{-6}$ m$^3$/s) for one hour at 400° C. The reactor temperature was then adjusted to 290° C. and the reactor purged with nitrogen.

CHF$_2$CF$_2$CH$_2$F was vaporized and fed to the reactor at such a rate as to maintain a contact time with the catalyst of 120 seconds. No nitrogen co-feed was present. Gas chromatographic analyses of the reactor effluent at three temperatures are listed in Table 3.

TABLE 3

| | GC Area Percent | | |
|---|---|---|---|
| Reactor Temp, °C. | CHF$_2$CF$_2$CH$_2$F | CHF$_2$CHFCHF$_2$ | E and Z-CHF$_2$CF=CHF |
| 275 | 72.3 | 5.5 | 22.0 |
| 325 | 40.8 | 6.9 | 51.7 |
| 375 | 27.0 | 3.2 | 68.9 |

Example 4

Hydrogenation of CHCl$_2$CF$_2$CF$_3$ and CHClFCF$_2$CClF$_2$

A commercial palladium on aluminum oxide catalyst (0.5% Pd/Al$_2$O$_3$, 10 cc, 12-20 mesh (1.68-0.84 mm)) was placed in a 30.5 cm×1.27 cm o.d. Hastelloy® tube. The tube was connected to a reactor system and surrounded with a electrically-heated furnace. The catalyst was first purged with nitrogen (25 sccm, 4.1×10$^{-7}$ m$^3$/s) for three hours as the temperature of the reactor was increased from 100° C. to 300° C. After cooling to 150° C., the catalyst was reduced with hydrogen (20 sccm, 3.3×10$^{-7}$ m$^3$/s) for three hours as the temperature of the reactor was increased from 100° C. to 300° C. After again cooling to 150° C. under a nitrogen purge, the catalyst was treated with a mixture of nitrogen and hydrogen fluoride according to the following sequence (flow rate N$_2$, flow rate H$_2$, time, temperature): 45 sccm (7.4×10$^{-7}$ m$^3$/s), 5 sccm (8.3×10$^{-8}$ m$^3$/s), 2 hours, 150° C.; 40 sccm (6.6×10$^{-7}$ m$^3$/s), 10 sccm (1.7×10$^{-7}$ m$^3$/s), 2 hours, 150° C.; 40 sccm (6.6×10$^{-7}$ m$^3$/s), 10 sccm (1.7×10$^{-7}$ m$^3$/s), 2 hours, 200° C.; 40 sccm (6.6×10$^{-7}$ m$^3$/s), 10 sccm (1.7×10$^{-7}$ m$^3$/s), 2 hours, 250° C.; 25 sccm (4.1×10$^{-7}$ m$^3$/s), 25 sccm (4.1×10$^{-7}$ m$^3$/s), 2 hours, 250° C. The flow of HF was then stopped and the catalyst purged with nitrogen (20 sccm, (3.3×10$^{-7}$ m$^3$/s) as the temperature was reduced to about 150° C. The catalyst was then used for several runs involving reactions with hydrogen and/or hydrogen fluoride and then reactivated by treatment with air (40 sccm (6.6×10$^{-7}$ m$^3$/s) for 2 hours at 300° C.) followed by nitrogen purging, treatment with hydrogen (50 sccm (8.3×10$^{-7}$ m$^3$/s) for 2 hours at 350° C.) and another nitrogen purging.

A mixture of HCFC-225 isomers comprising CF$_3$CF$_2$CHCl$_2$ (HCFC-225ca, about 41%) and CClF$_2$CF$_2$CHClF (HCFC-225cb, about 59%) and hydrogen (1:3 molar ratio) was fed to the above catalyst at 300° C.; the contact time was nominally 30 seconds. The analysis of the reactor effluent as determined by GC-MS is given in TABLE 4.

Example 5

Hydrogenation of HCFC-225's

A mixture of HCFC-225 isomers and hydrogen (1:5 molar ratio) was fed to the catalyst described in Example No. 4 at 350° C.; the contact time was nominally 20 seconds. The analysis of the reactor effluent as determined by GC-MS is given in TABLE 4.

TABLE 4

| EX. NO. | HFC-245cb | HFC-1234yf | HFC-263fb | HFC-254eb | HFC-245ca | HCFC-235cc | HCFC-235cb | HCFC-235ca | HCFC-225ca/cb |
|---|---|---|---|---|---|---|---|---|---|
| | | | | GC area percent | | | | | |
| 4 | 41.1 | 0.1 | 0.8 | 0.7 | 1.5 | 14.5 | 8.8 | 4.4 | 26.5 |
| 5 | 31.4 | 0.6 | 3.9 | 1.6 | 1.0 | 8.0 | 7.3 | 2.8 | 40.4 |

What is claimed is:

1. A process for making $CF_3CF=CH_2$, consisting essentially of:
   a) reacting $CHCl_2CF_2CF_3$, and optionally $CHClFCF_2CClF_2$ with $H_2$ in the presence of a catalytically effective amount of a hydrogenation catalyst to form a product mixture comprising $CF_3CF=CH_2$; and
   b) recovering $CF_3CF=CH_2$, from said product mixture formed in (a).

2. The process of claim 1, wherein the hydrogenation catalyst used in (a) comprises palladium supported on alumina, fluorided alumina, aluminum fluoride or a mixture thereof.

* * * * *